United States Patent
Perry et al.

(10) Patent No.: US 12,294,825 B2
(45) Date of Patent: *May 6, 2025

(54) WIRELESS EAR BUD SYSTEM WITH POSE DETECTION

(71) Applicant: Apple Inc., Cupertino, CA (US)

(72) Inventors: Daniel J. Perry, San Jose, CA (US); Maulik V. Choksi, Cupertino, CA (US); Wei-Yang Sun, San Francisco, CA (US)

(*) Notice: Subject to any disclaimer, the term of this patent is extended or adjusted under 35 U.S.C. 154(b) by 267 days.

This patent is subject to a terminal disclaimer.

(21) Appl. No.: 18/153,631

(22) Filed: Jan. 12, 2023

(65) Prior Publication Data

US 2023/0143987 A1    May 11, 2023

Related U.S. Application Data

(60) Continuation of application No. 17/514,503, filed on Oct. 29, 2021, now Pat. No. 11,601,743, which is a
(Continued)

(51) Int. Cl.
*H04R 1/10* (2006.01)
*A61B 5/00* (2006.01)
(Continued)

(52) U.S. Cl.
CPC .......... *H04R 1/1041* (2013.01); *A61B 5/1116* (2013.01); *A61B 5/1123* (2013.01); *A61B 5/486* (2013.01); *A61B 5/6817* (2013.01); *A61B 5/741* (2013.01); *G06F 3/165* (2013.01); *G06F 3/167* (2013.01); *H04R 1/1016* (2013.01); *A61B 5/0002* (2013.01); *A61B 2562/0219* (2013.01); *H04R 2420/07* (2013.01)

(58) Field of Classification Search
CPC . H04R 1/1041; H04R 1/1016; H04R 2420/07
USPC .......................................... 381/74, 26, 11, 12
See application file for complete search history.

(56) References Cited

U.S. PATENT DOCUMENTS

| 8,243,946 B2 | 8/2012 | Burge et al. | |
| 8,655,004 B2 * | 2/2014 | Prest | G06F 3/165 381/380 |

(Continued)

*Primary Examiner* — William J Deane, Jr.
(74) *Attorney, Agent, or Firm* — Treyz Law Group, P.C.; G. Victor Treyz; Joseph F. Guihan

(57) ABSTRACT

Ear buds may have sensors to gather orientation information such as accelerometer measurements during user movements. A host electronic device may communicate wirelessly with the ear buds and may form part of an ear bud system that supplies the user with coaching and feedback while evaluating user performance of a head movement routine or other exercise routine. During operation, the ear buds may gather accelerometer data in a first reference frame such as a reference frame associated with the ear buds and may use a rotation matrix to rotate the data in the first reference frame into a second reference frame such as a neutral reference frame with a fixed orientation to the earth. The data in the neutral reference frame may be analyzed using a user head pose look-up table to categorize measured user head positions as corresponding to respective user head poses.

15 Claims, 7 Drawing Sheets

Related U.S. Application Data continuation of application No. 16/897,524, filed on Jun. 10, 2020, now abandoned, which is a continuation of application No. 16/364,776, filed on Mar. 26, 2019, now Pat. No. 10,715,902, which is a division of application No. 15/914,554, filed on Mar. 7, 2018, now Pat. No. 10,277,973.

(60) Provisional application No. 62/480,214, filed on Mar. 31, 2017.

(51) Int. Cl.
*A61B 5/11* (2006.01)
*G06F 3/16* (2006.01)

(56) References Cited

U.S. PATENT DOCUMENTS

| | | | |
|---|---|---|---|
| 9,237,393 B2* | 1/2016 | Abrahamsson | H04R 1/1041 |
| 9,374,647 B2 | 6/2016 | Han et al. | |
| 9,497,534 B2 | 11/2016 | Prest et al. | |
| 9,554,607 B2 | 1/2017 | Mack et al. | |
| 9,579,060 B1* | 2/2017 | Lisy | A61B 5/4803 |
| 9,838,776 B2* | 12/2017 | Broadley | H04R 1/1066 |
| 9,950,239 B1 | 4/2018 | Harvey | |
| 10,277,973 B2 | 4/2019 | Perry et al. | |
| 10,291,975 B2* | 5/2019 | Howell | H04R 1/1041 |
| 10,692,489 B1* | 6/2020 | Grizzel | G06F 3/167 |
| 10,715,902 B2* | 7/2020 | Perry | A61B 5/1123 |
| 2008/0076972 A1 | 3/2008 | Dorogusker et al. | |
| 2009/0097689 A1* | 4/2009 | Prest | H04R 1/028 381/370 |
| 2010/0020998 A1 | 1/2010 | Brown et al. | |
| 2010/0074460 A1 | 3/2010 | Marzetta | |
| 2010/0150355 A1 | 6/2010 | Kon et al. | |
| 2012/0114132 A1 | 5/2012 | Abrahamsson et al. | |
| 2012/0114154 A1 | 5/2012 | Abrahamsson | |
| 2013/0311176 A1 | 11/2013 | Brown et al. | |
| 2014/0025287 A1 | 1/2014 | Christensen | |
| 2014/0062842 A1* | 3/2014 | Tachibana | H04M 1/6058 345/8 |
| 2015/0003634 A1 | 1/2015 | Yliaho et al. | |
| 2015/0077234 A1 | 3/2015 | Fullam | |
| 2016/0000373 A1* | 1/2016 | Karavirta | A61B 5/02405 702/19 |
| 2016/0007112 A1* | 1/2016 | Broadley | H04R 1/1066 381/72 |
| 2016/0007933 A1* | 1/2016 | Duddy | A61B 5/1123 600/595 |
| 2016/0014539 A1 | 1/2016 | Yeh | |
| 2017/0078785 A1 | 3/2017 | Qian et al. | |
| 2017/0104928 A1* | 4/2017 | Chase | H04N 5/77 |
| 2017/0163784 A1* | 6/2017 | Frazier Fields | H04W 4/02 |
| 2017/0180842 A1 | 6/2017 | Boesen | |
| 2017/0209095 A1 | 7/2017 | Wagner et al. | |
| 2017/0216671 A1 | 8/2017 | Wisbey et al. | |
| 2018/0116561 A1 | 5/2018 | Jo et al. | |
| 2018/0124495 A1 | 5/2018 | Boesen | |
| 2018/0125423 A1* | 5/2018 | Chang | A61B 5/6803 |
| 2018/0146319 A1 | 5/2018 | Benattar | |
| 2018/0338199 A1 | 11/2018 | Boesen et al. | |

* cited by examiner

WIRELESS EAR BUD SYSTEM WITH POSE DETECTION

This application is a continuation of application Ser. No. 17/514,503, filed Oct. 29, 2021, which is a continuation of application Ser. No. 16/897,524, filed Jun. 10, 2020, which is a continuation of application Ser. No. 16/364,776, filed Mar. 26, 2019, which is a division of application Ser. No. 15/914,554, filed Mar. 7, 2018, which claims the benefit of provisional patent application No. 62/480,214, filed Mar. 31, 2017, which are hereby incorporated by reference herein in their entireties.

BACKGROUND

This relates generally to electronic devices, and, more particularly, to wearable electronic devices such as ear buds.

Electronic devices such as laptop computers and cellular telephones are popular portable devices. Wearable devices such as wristwatch devices and ear buds can provide enhanced freedom of movement. For example, wireless ear buds can be used to play audio content for a user of an electronic device such as a cellular telephone or computer without cumbersome cables.

It would therefore desirable to be able to provide improved wearable electronic devices such as improved wireless ear buds.

SUMMARY

A system is provided in which electronic equipment such as ear buds are used to provide audio information to a user while using orientation sensors such as accelerometers to gather orientation information. A host electronic device may communicate wirelessly with the ear buds. During operation, the ear buds may be used to provide a user with exercise routine coaching such as audible instructions while a user is performing an exercise routine such as a head movement routine. The head movement routine may involve, for example, moving the user's head into a sequence of predefined head poses (e.g., left tilt, forward tilt, right tilt, and back tilt).

While being coached, the ear buds may gather accelerometer data in a first reference frame such as a reference frame associated with the ear buds and may use a rotation matrix to rotate the data in the first reference frame into a second reference frame such as a neutral reference frame. The data in the neutral reference frame may be analyzed using a user head pose look-up table with threshold accelerometer values for different head poses to categorize the data as corresponding to respective user head poses.

Feedback such as audible feedback may be provided to a user based on evaluation of user performance of the head movement routine. Other suitable actions may be taken such as issuing performance reports and alerts. If desired, additional sensors may be used in gathering orientation data during user movement routines and additional evaluation, guidance, and feedback operations may be performed.

DETAILED DESCRIPTION

Wearable electronic devices such as ear buds may be used to gather information on the behavior of a user. For example, ear buds may include sensors such as orientation sensors that gather information on the orientation of a user's head. In some scenarios, the ear buds may form part of a system that uses the orientation information or other sensor information from the ear buds. For example, ear bud sensor data may be used in a system in which ear buds communicate wirelessly with a host device.

Figure 1:
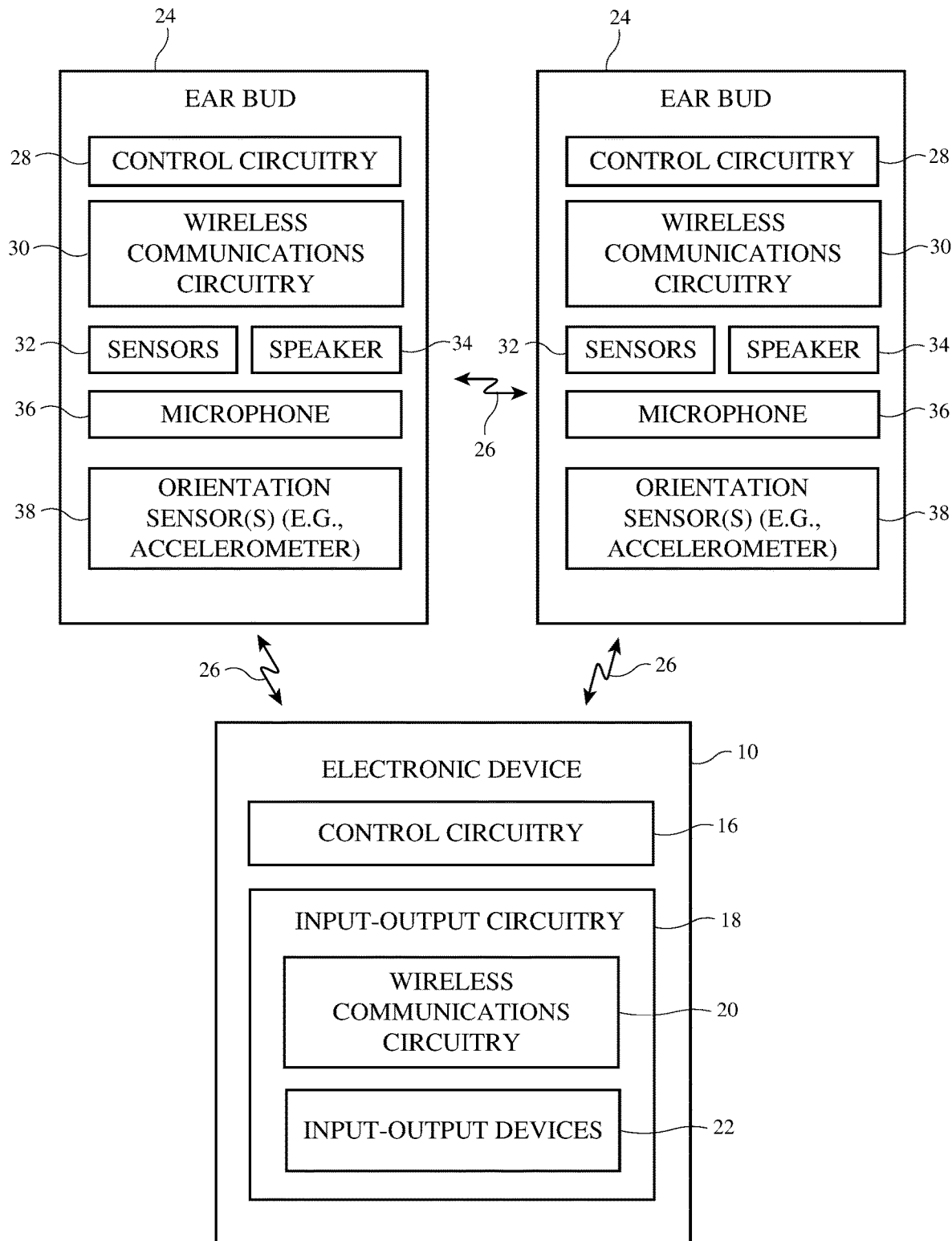
FIG. 1 is a schematic diagram of an illustrative system including electronic equipment that communicates wirelessly with wearable electronic devices such as wireless ear buds in accordance with an embodiment.

An illustrative system of the type that may include wearable electronic equipment such as one or more ear buds is shown in FIG. 1. As shown in FIG. 1, system 8 may include one or more host devices such as host device 10 and one or more wearable devices such as ear buds 24. Host electronic device 10 of FIG. 1 may be a cellular telephone, may be a computer, may be a wristwatch device, may be a head-mounted display device, may be other wearable equipment, may be part of an embedded system (e.g., a system in a plane or vehicle), may be part of a home network, may be a television or set-top box, may be a voice-controlled assistant device, may be a portable device or a device that is not portable, may be other suitable electronic equipment, or may be a network based on a group of such devices.

As shown in FIG. 1, electronic device 10 may have control circuitry 16. Control circuitry 16 may include storage and processing circuitry for supporting the operation of device 10. The storage and processing circuitry may include storage such as hard disk drive storage, nonvolatile memory (e.g., flash memory or other electrically-programmable-read-only memory configured to form a solid state drive), volatile memory (e.g., static or dynamic random-access-memory), etc. Processing circuitry in control circuitry 16 may be used to control the operation of device 10. The processing circuitry may be based on one or more microprocessors, microcontrollers, digital signal processors, baseband processors, power management units, audio chips, application specific integrated circuits, etc.

Device 10 may have input-output circuitry 18. Input-output circuitry 18 may include wireless communications circuitry 20 (e.g., radio-frequency transceivers) for supporting communications with wireless wearable devices such as ear buds 24 or other wireless wearable electronic devices via wireless links 26. Circuitry 20 may include satellite navigation system circuitry (e.g., Global Positioning System receiver circuitry) for making measurements of geographic location and velocity. Ear buds 24 may have corresponding wireless communications circuitry 30 for supporting communications with circuitry 20 of device 10 and, if desired, for making measurements of geographic location and velocity. In some configurations, ear buds 24 may use wireless circuitry 30 to communicate with each other directly or through device 10 over wireless links 26. Devices such as ear buds 24 may also communicate with devices such as device 10 using wired connections. In general, the devices that communicate with device 10 may be any suitable portable and/or wearable equipment. Configurations in which system 8 has wireless wearable devices such as ear buds 24 are sometimes described herein as an example.

Input-output circuitry in device 10 such as input-output devices 22 may be used to allow data to be supplied to device 10 and to allow data to be provided from device 10 to external devices. One or more of these input-output devices may also be included in ear buds 24 and controlled using control circuitry 28.

Input-output devices 22 may include buttons, joysticks, scrolling wheels, touch pads, key pads, keyboards, microphones, speakers, displays (e.g., touch screen displays), tone generators, haptic output devices such as electromechanical actuators and vibrators (e.g., piezoelectric vibrating components, etc.), cameras, sensors, light-emitting diodes and other status indicators, data ports, etc. The sensors in input-output devices 22 may include orientation sensors (e.g., accelerometers, gyroscopes, and/or magnetic sensors such as compasses), force sensors (e.g., capacitive force sensors, piezoelectric force sensors, strain gauges, etc.), touch sensors such as capacitive touch sensors (e.g., in track pads, displays, or buttons or other stand-alone devices), infrared proximity sensors and/or other light-based proximity sensors, capacitive proximity sensors, color-sensing and light-intensity-sensing ambient light sensors, audio sensors (e.g., diaphragms in microphones), digital image sensors (e.g., sensors in cameras), range-detection sensors such as LIDAR (light detection and ranging) sensors, radar, and echolocation sensors, radio-frequency sensors (e.g., circuitry that allows system 8 to gather position information and/or orientation information based on triangulation techniques, time-of-flight techniques, received signal strength techniques, etc.), free-space gesture sensors (e.g., camera-based, laser-scanner based, acoustic, capacitive, etc.), eye tracking sensors, temperature sensors, gas sensors, particulate sensors, humidity sensors, pressure sensors (e.g., to measure atmospheric pressure), and/or other sensors. A user can control the operation of device 10 by supplying commands through input-output devices 22 and may receive status information and other output from device 10 using the output resources of input-output devices 22. If desired, some or all of these input-output devices may be incorporated into ear buds 24.

Each ear bud 24 may have control circuitry 28 (e.g., control circuitry such as control circuitry 16 of device 10), wireless communications circuitry 30 (e.g., one or more radio-frequency transceivers for supporting wireless communications over links 26), may have one or more sensors 32 (e.g., sensors of the type that may be included in device 10), and may have additional components such as speakers 34 and microphones 36. Ear buds 24 may include orientation sensors 38 (e.g., accelerometers, gyroscopes, and/or compasses).

Sensors 38, which may sometimes be referred to as accelerometers, may gather data on the orientation of ear buds 24 dynamically, so that the components of system 8 may measure the orientation of a user's head when a user is wearing one or more of ear buds 24. Speakers 34 may play audio into the ears of a user. Microphones 36 may gather audio data such as the voice of a user who is making a telephone call and can detect voice commands. Proximity sensors in sensors 32 may emit and/or detect light and/or may include capacitive proximity sensor circuitry to generate proximity output data based on measurements by capacitance sensors (as examples). Proximity sensors may be used to detect the presence of a portion of a user's ear to ear bud 24 and/or may be triggered by the finger of a user (e.g., when it is desired to use a proximity sensor as a capacitive button or when a user's fingers are gripping part of ear bud 24 as ear bud 24 is being inserted into the user's ear). User input such as intentional taps on ear buds 24 may also be detected using accelerometers (sensors 38) and used in controlled ear buds 24 and/or host 10.

Sensors 38 may detect when ear buds 24 are in motion or are at rest. In some arrangements, information from sensor 38 can be used to evaluate user performance of an exercise routine such as a head movement routine (e.g., whether a user is satisfactorily following a predetermined exercise routine such as a head movement routine in which the user intentionally places their head in various stretch positions (e.g., head tilted to left, right, forward, or back). These stretch positions, which may sometimes be referred to as user head poses, user head tilts, neck stretches, poses, etc., may be used to help stretch and relax the muscles in a user's upper body.

Using gyroscope and/or compass circuitry in sensors 38, sensors 38 can also monitor whether a user is following a predetermined exercise routine in which the user's head is rolled, twisted, and/or turned smoothly through various orientations. When used in combination with wrist watch devices and other wearable devices on other portions of a user's body (e.g., a wrist watch worn on a user's arms, legs, etc.) in system 8, system 8 can use ear buds 24 in detecting more complex user movements (e.g., Yoga positions and/or other exercise movements involving multiple portions of the user's body). In these configurations and other configurations for system 8, host electronic device 10 may serve as a master device and ear buds 24 and/or other wearable electronic devices on the body of the user may serve as slave devices or other control architectures may be used (e.g., distributed networks in which the devices in system 8 serve as peer devices, networks in which ear buds 24 or other wearable devices serve as master(s), etc.).

Control circuitry in system 8 such as control circuitry 28 in ear buds 24 and control circuitry 16 of device 10 may be used to run software on ear buds 24 and device 10 and/or other devices in system 8. During operation, the software running on control circuitry 28 and/or 16 may be used in gathering sensor data, user input, and other input and may be used in taking suitable actions in response to detected conditions. As an example, control circuitry 28 and/or control circuitry 16 may be used in providing a user with audio exercise routine guidance (e.g., verbal commands such as "perform left stretch now" or other head pose guidance, other audible information such as a sequence of chimes, etc.) while determining the orientation of a user's head and providing feedback based on an analysis of whether the user is satisfactorily completing a desired exercise routine. Music and other content may also be provided.

In some scenarios, ear buds 24 may be used in handling other audio information, such as audio signals for cellular telephone calls. Control circuitry 28 and/or 16 may also be used in coordinating operation between a pair of ear buds 24 that are paired with a common host device (e.g., device 10), handshaking operations, calibration operations, and/or other maintenance and support operations.

In some situations, it may be desirable to accommodate stereo playback from ear buds 24. This can be handled by designating one of ear buds 24 as a primary ear bud and one of ear buds 24 as a secondary ear bud. The primary ear bud may serve as a slave device while device 10 serves as a master device. A wireless link between device 10 and the primary ear bud may be used to provide the primary ear bud with stereo content. The primary ear bud may transmit one of two channels of stereo content to the secondary ear bud for communicating to the user (or this channel may be transmitted to the secondary ear bud from device 10). Microphone signals (e.g., voice information from a user during a telephone call) may be captured by using microphone 36 in the primary ear bud and conveyed wirelessly to device 10.

Figure 2:
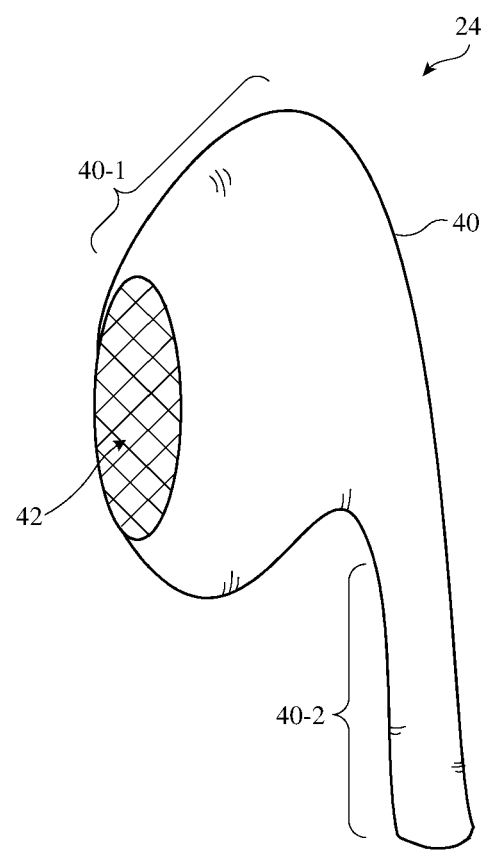
FIG. 2 is a perspective view of an illustrative ear bud in accordance with an embodiment.

FIG. 2 is a perspective view of an illustrative ear bud. As shown in FIG. 2, ear bud 24 may include a housing such as housing 40. Housing 40 may have walls formed from plastic, metal, ceramic, glass, sapphire or other crystalline materials, fiber-based composites such as fiberglass and carbon-fiber composite material, natural materials such as wood and cotton, other suitable materials, and/or combinations of these materials. Housing 40 may have a main portion such as main body 40-1 that houses audio port 42 and a stem portion such as stem 40-2 or other elongated portion that extends away from main body portion 40-1. During operation, a user may grasp stem 40-2 and, while holding stem 40-2, may insert main portion 40-1 and audio port 42 into the ear. Audio ports such as audio port 42 may be used for gathering sound for a microphone and/or for providing sound to a user (e.g., audio associated with a telephone call, media playback, an audible alert, etc.). For example, audio port 42 of FIG. 2 may be a speaker port that allows sound from speaker 34 (FIG. 1) to be presented to a user. Sound may also pass through additional audio ports (e.g., one or more perforations may be formed in housing 40 to accommodate microphone 36).

Figure 3:
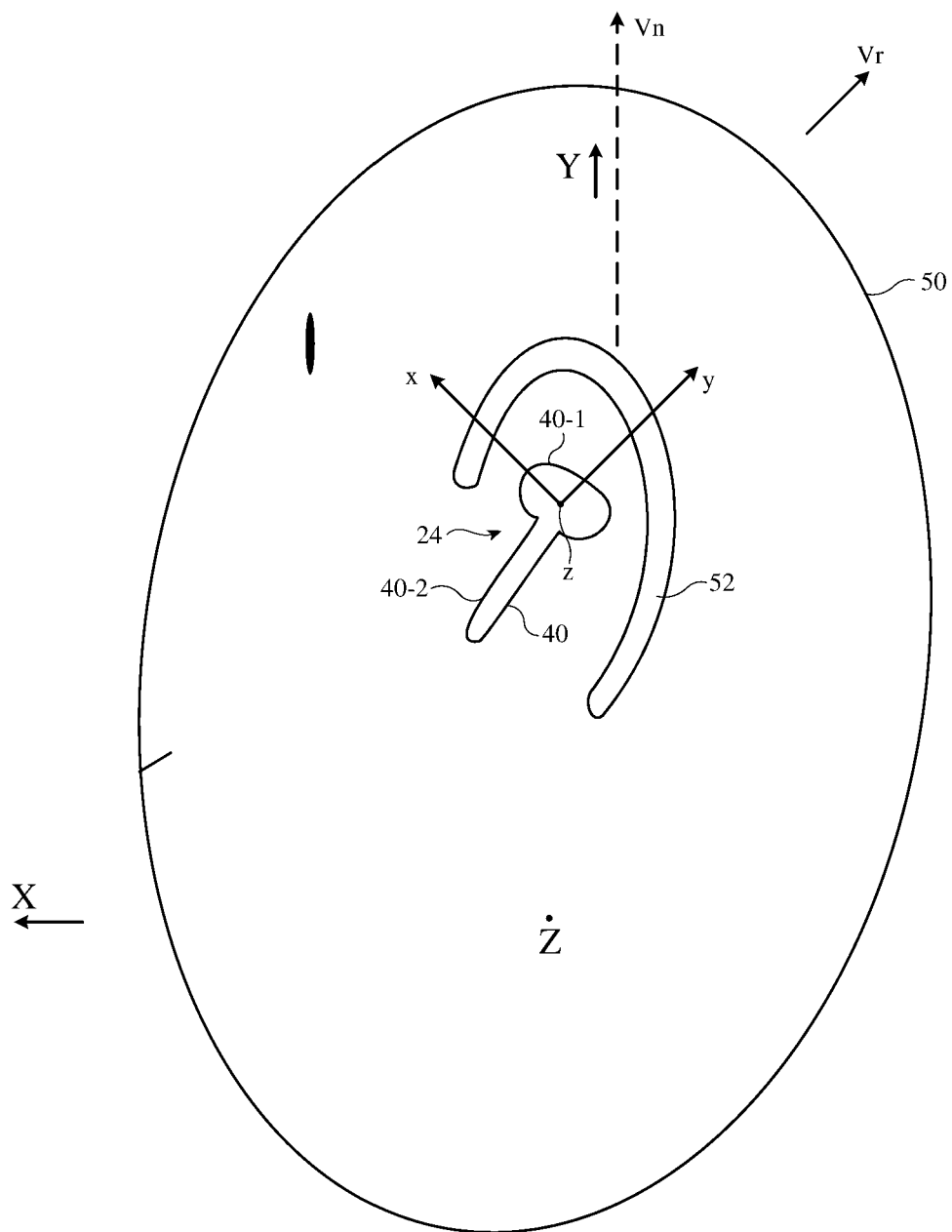
FIG. 3 is a side view of an illustrative ear bud located in an ear of a user in accordance with an embodiment.

FIG. 3 is a diagram showing how ear bud 24 may be worn in ear 52 of user's head 50. Axis y (and perpendicular axes x and z) form an ear-bud-centric coordinate system (user's head frame of reference) that the accelerometer (and/or other orientation sensor circuitry) in ear bud 24 may use in collecting three respective channels of accelerometer data (e.g., x-axis accelerometer signals, y-axis accelerometer signals, and z-axis accelerometer signals). As shown in FIG. 3, when main portion 40-1 of ear bud 24 is being worn in ear 52, elongated ear bud body 40 (e.g., stem 40-2) may extend along an axis y that is not generally perpendicular to the surface of the earth. During operation, control circuitry in system 8 may rotate raw three-axis accelerometer data to place this data into a neutral coordinate system such as the illustrative X-Y-Z coordinate system of FIG. 3. For example, raw body-frame-of-reference accelerometer data such as raw data vector Vr, which includes three channels of body frame accelerometer data (x, y, z), may be transformed into neutral-frame-of-reference data such as neutral frame vector Vn, which includes three adjusted accelerometer values (X, Y, Z), by multiplying the body frame vector Vr by a rotation matrix R.

This transforms the raw accelerometer data Vr into data Vn for comparison to predefined threshold limits. For example, when a user's head is oriented in its normal upright position along vertical axis Y of FIG. 3, Vn will be equal to 0, 1, 0, because all accelerometer data in the reference frame will be in the vertical Y axis (perpendicular to the surface of the earth) and none will be in the horizontal X and Z axes (parallel to the surface of the earth). The limits to which the neutral frame accelerometer data is compared may be, for example, look-up-table threshold values that define the head orientations that correspond to various respective head poses.

Figure 4:
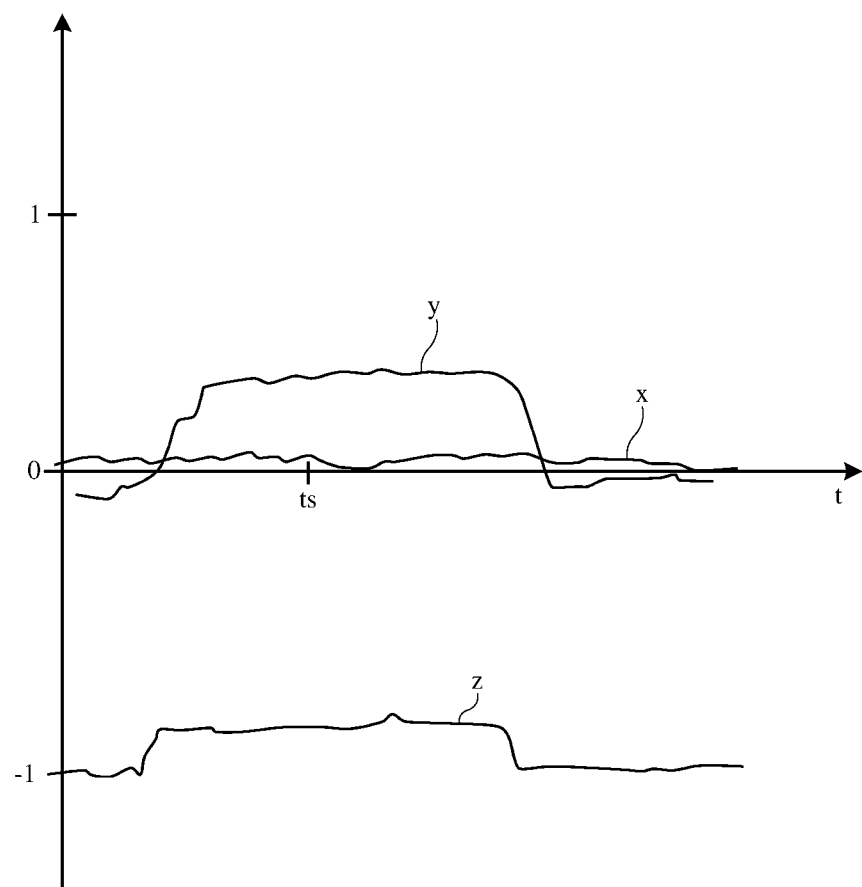
FIG. 4 is a graph of illustrative ear bud accelerometer output signals gathered while a user is performing a head pose in accordance with an embodiment.

FIG. 4 is a graph of illustrative raw accelerometer data (x, y, z) during a head movement such as a right head tilt (right pose). If desired, gyroscope data or other orientation system data may be gathered to measure the amount (e.g., a value in degrees or other units) by which a user has rotated head 50 about vertical axis Y. Compass data may be used to enhance orientation measurement accuracy, if desired.

Figure 5:
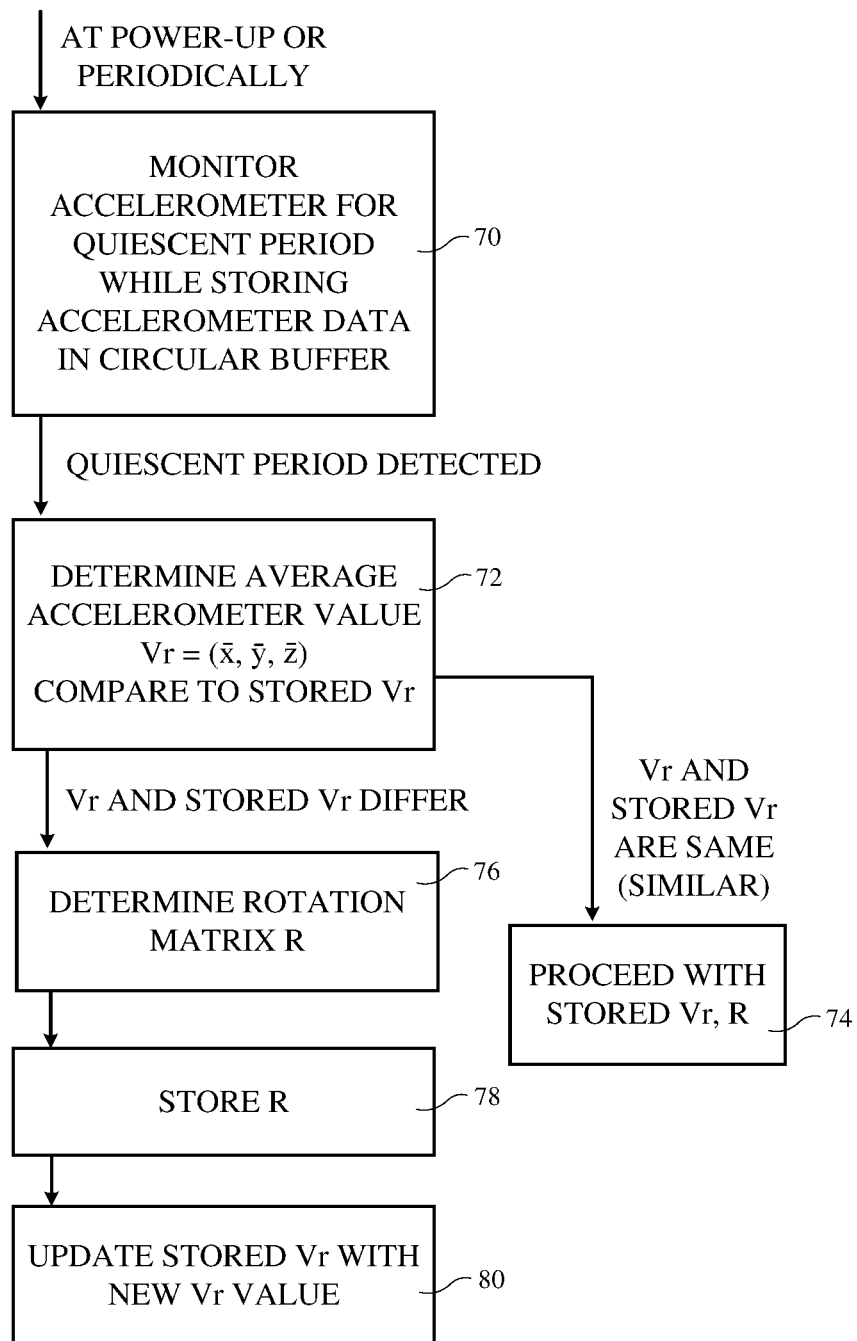
FIG. 5 is a flow chart of illustrative operations involved in calibrating an ear bud orientation sensor in accordance with an embodiment.

Illustrative operations involved in calibrating ear buds 24 to produce rotation matrix R are shown in the flow chart of FIG. 5.

Ear buds 24 may be calibrated each time device 10 is powered up, periodically (e.g., according to a predetermined schedule or refresh time period), and/or when other calibration conditions are satisfied.

During the operations of block 70, control circuitry 28 may gather accelerometer data with sensor(s) 38 and may store this accelerometer data in a circular data buffer. The accelerometer data that is being gathered may be compared to predetermined threshold values to determine whether ear buds 24 are in a quiescent state in which the user is not moving significantly. Control circuitry 28 can conclude that ear buds 24 and the associated accelerometer data are quiescent when the accelerometer data is less than the predetermined threshold values for a predetermined period of time (e.g., 0.3-1 s, at least 0.1 s, at least 1 s, at least 5 s, less than 30 s, less than 10 s, or other suitable time). When the user's head 50 is stationary or nearly stationary, and control circuitry 28 determines that ear buds 24 are being used in a quiescent period (quiescent state), processing can proceed to block 72.

During the operations of block 72, the contents of the circular data buffer can be processed to determine the average of the accelerometer values in all or part of the circular data buffer (vector Vr). For example, the x-axis accelerometer values can be averaged to produce an average x value, the y-axis accelerometer values can be averaged to produce an average y value, and the z-axis accelerometer values can be averaged to produce an average z value. This average vector corresponds to the expected accelerometer output when the user's head is in its normal upright (vertical) orientation. Vector Vr can be compared to a previously stored value of Vr to determine whether there is a significant difference between these values (more than a threshold amount). If the presently measured value of Vr and the stored value of Vr are within the threshold amount, the stored value of Vr and associated stored value of rotation matrix R can be retained.

In response to detecting that the value of Vr that was produced during block 72 and the stored value of Vr differ by more than the threshold amount (e.g., the stored value of Vr is empty because calibration operations are being performed for the first time or the new and stored Vr values otherwise differ by more than the threshold), control circuitry 28 can perform the operations of block 76. During block 76, control circuitry 28 can compute rotation matrix R from equations 1, 2, 3, and 4, with angles rotated about the neutral axis (theta_x, theta_y, and theta_z) from accelerometer data Vr.

$$R=(R\_x)(R\_y)(R\_z) \tag{1}$$

$$R\_x=[[1,0,0],[0, \cos(\text{theta}\_x),-\sin(\text{theta}\_x)],[0, \sin(\text{theta}\_x), \cos(\text{theta}\_x)]] \tag{2}$$

$$R\_y=[[\cos(\text{theta}\_y),0, \sin(\text{theta}\_y)],[0,1,0],[-\sin(\text{theta}\_y),0, \cos(\text{theta}\_y)]] \tag{3}$$

$$R\_z=[[\cos(theta\_z),-\sin(theta\_z),0],[\sin(theta\_z), \cos(theta\_z),0],[0,0,1]] \quad (4)$$

In equations 1, 2, 3, and 4, angles theta_x, theta_y, and theta_z are determined from sensor data Vr and rotation matrix R is the matrix that rotates data Vr to vector Vn (e.g., Vn=RVr) where Vn is a vector (e.g., 0, 1, 0) associated with a neutral reference frame. (The neutral reference frame may be characterized by neutral-frame X, Y, and Z axes where the X-Z plane is parallel to the surface of the earth, whereas the body reference frame may be characterized by than body-frame x, y, and z axes where y is directed along the length of the ear bud housing). The computed value of R can be stored in storage in control circuitry 28 during the operations of block 78. During the operations of block 80, control circuitry 28 can store the newly computed value of Vr in place of the previously stored value of Vr (e.g., circuitry 28 may update Vr).

Figure 6:
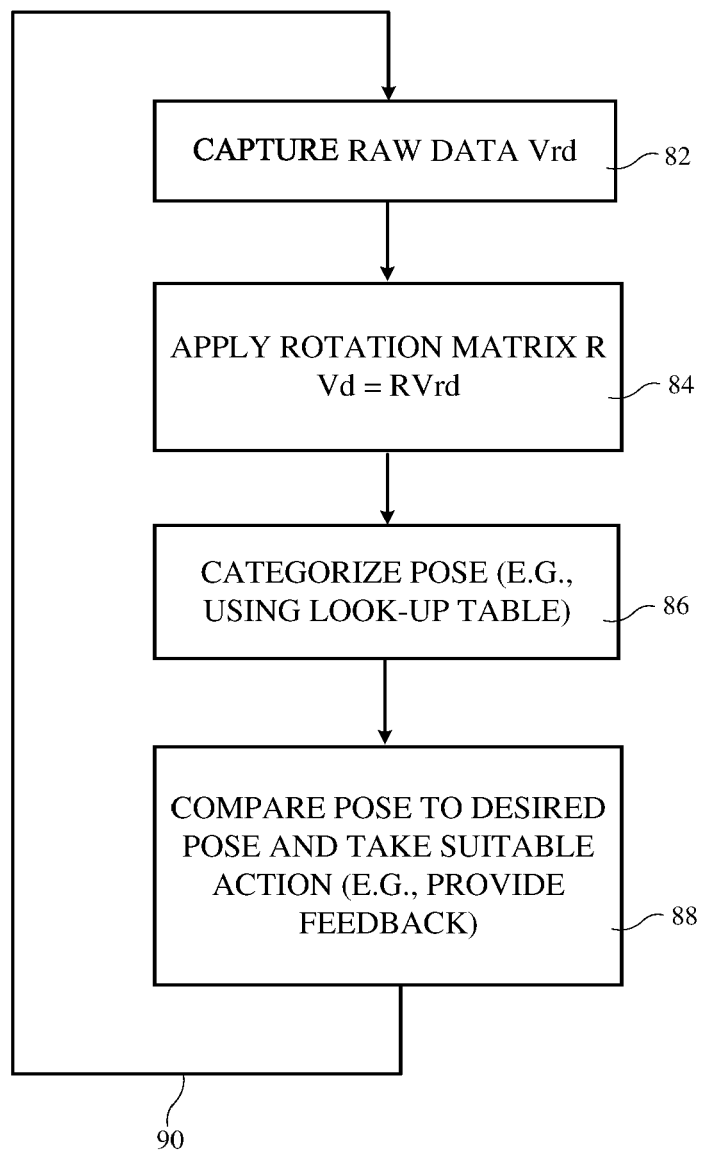
FIG. 6 is a flow chart of illustrative operations involved in operating a system with wireless ear buds that include orientation sensor circuitry such as accelerometer circuitry in accordance with an embodiment.

Illustrative operations involved in using system 8 while a user is performing a head stretching exercise are shown in FIG. 6.

During the operations of block 82, control circuitry 28 may use sensor 38 (e.g., an accelerometer) to gather raw accelerometer data Vrd. If desired, filtering operations may be performed while capturing data Vrd. For example, data Vrd may be collected by maintaining running averages of the output of each sensor channel for a predetermined period of time, thereby averaging out high frequency noise. Raw data Vrd may be gathered at 100-200 Hz or other suitable data capture rate.

During the operations of block 84, control circuitry 28 may apply rotation matrix R to data Vrd to transform orientation measurement Vrd from the user's body reference frame to rotated (calibrated) orientation measurement Vd in the neutral reference frame (e.g., Vd is set equal to RVrd).

During the operations of block 86, control circuitry 28 may process data Vd to determine whether a predefined pose is being performed. A look-up table maintained in storage in control circuitry 28 or other suitable data structure or function may be used in analyzing data Vd to determine whether the head of user has been moved into a position associated with a desired pose. Consider, as an example, a scenario in which a user is performing a routine in which the user is expected to sequentially tilt to the left, to the front, to the right, and to the back. Data Vd may fall within predefined limits associated with a left pose (e.g., a neck stretch to the left), a front pose (e.g., a forward neck stretch), a right pose (e.g., a neck stretch to the right), or a back pose (e.g., a neck stretch in which the user's head tilts backwards). Separate rows in the look-up table may be used in storing threshold data values in the neutral reference frame that correspond to each of these poses. By comparing Vd to the look-up table information, the pose being performed by the user can be characterized. If, for example, the user's head is tilted to the left in a left pose, Vd will fall within the predetermined accelerometer values (e.g., maximum and minimum values for each of the accelerometer channels) associated with a left pose, so the user's head orientation may be characterized as a left pose.

During the operations of block 88, after categorizing the user's head orientation by determining which pose is being performed, the pose that is being performed can be compared to a desired sequence of poses associated with a head movement exercise routine. If, for example, the user was expected to perform neck stretches in a left-forward-right-backward order, control circuitry 28 may, during the operations of block 88 determine whether the pose that was identified during the operations of block 86 falls within the desired pose sequence and has occurred in a timely fashion. If a pose is performed unsatisfactorily (e.g., in the wrong order, at the wrong time, etc.), the user may be provided with an alert (e.g., negative feedback in the form of an audible tone indicative of an unsatisfactory pose such as a buzzer sound, spoken feedback, etc.). Positive feedback such as a pleasant chime or other positive audio feedback can be played back to the user with ear buds 24 in the event that control circuitry 28 determines that the desired pose has been satisfactorily performed. Head pose guidance may be provide to a user during the operations of FIG. 6. For example, control circuitry 28 may use speaker 34 to provide the user with instructions such as "tilt left now" that serve as real-time user head pose guidance.

In evaluating poses during the operations of block 88 to determine whether a predetermined exercise routine is being performed satisfactorily, control circuitry 28 may require that the user perform each pose within a predetermined time slot (e.g., in a series of 1 second time slots accompanied by a 1 Hz sequence of audible coaching clicks), may require that each pose be performed within a given time limit following detection of successful completion of a previous pose (e.g., control circuitry 28 may require that the forward-tilting pose be performed within 1 s of successful completion of the leftward-tilting pose, etc.), or other pose performance criteria may be established. Pose patterns may involve circular sequences of head poses and/or other patterns (back and forth, side to side, diagonal, etc.). As indicated by line 90, processing can loop back to block 82 after block 88 so that additional accelerometer data can be captured and analyzed.

If desired, neck movements can be categorized by using sensor 38 (e.g., a compass and/or gyroscope in sensor 38) to measure head rotation in addition to or instead of measuring head tilt. In this way, stretching routines can be analyzed that involve head rolls and other movements involving head rotation in addition to head tilts. The operations of FIGS. 5 and 6 may be performed using control circuitry 28 of ear buds 24 and/or control circuitry 16 of one or more devices such as device 10.

Other sensors can be used to gather information on the user's head orientation and movement if desired. Sensors in host 10 and/or other devices that are wirelessly communicating with ear buds 24 and/or host 10 can also be used in monitoring the movements of the user. For example, wearable devices such as wristwatch devices, health bands, shoes, gloves, and other devices can be used to measure where the user's hands, arms, feet, legs, and other body parts are moving. This allows ear buds 24, host 10, and/or other equipment in system 8 to determine whether a user is performing desired yoga poses, is walking or running with desired characteristics, etc.

Device 10 or other equipment in system 8 can provide visual output such as visual pose guidance or other coaching information that assists the user in performing a desired routine. For example, a cellular telephone, tablet computer, desktop computer, television, or other device with a display may display still and/or moving images illustrating desired poses (e.g., images showing a real person or a graphic representation of a person tilting their head to the left when a left pose is desired). If desired, visual guidance can be provided using text or other information (e.g., "perform left pose now").

Feedback may be provided to the user with device 10 in addition to or instead of using ear buds 24 to provide feedback. For example, a green icon may be displayed when a pose has been successfully performed and a red icon may be displayed when a pose has not been successfully performed. Performance grades (e.g., A+) may be provided when a routine is complete and/or grades or other evaluation results may be displayed or otherwise provided to a user during a routine.

If desired, sensors 38 may include optical sensors. For example, a camera in ear buds 25 may gather information on a user's environment and can be used to monitor head movement. Head-mounted LIDAR (on a head-mounted device 10 and/or ear buds 24), image processing from external cameras (e.g., a camera on device 10 in system 8), echolocation (sonar), and radio-frequency measurement techniques may also be used in system 8 to monitor movement of the user. For example, device 10 may emit radio-frequency signals, acoustic signals, or other signals that are used in measuring the position of the user's head or other body parts. In configurations in which antennas are worn on the body of the user, radio-frequency triangulation techniques may be used in measuring user movement.

If desired, user movement during exercise routines or other activities that involve user movement may be measured using devices other than ear buds 24 (e.g., devices that include the circuitry of ear buds 24 in a different form factor). These devices may include, for example, hats, helmets, earrings, headbands, glasses, head-mounted displays, or other headwear with sensors 38. These devices may also include necklaces, scarves, shirts, jackets, shoes, and other wearable items. The processing algorithms implemented by system 8 may use sensors such as gyroscopes and/or compasses (magnetic sensors) to measure head rotation and/or accelerometer data from one or more accelerometers may be processed to measure head rotation (e.g., based on inertial measurements). In some configurations, the control circuitry of system 8 may process images captured with an external camera or a body-mounted camera. Strain-gauge measurements and/or other measurements of force and deformation in an item such as a scarf that is worn around a user's neck may be analyzed to measure head movement. User commands may be provided using voice, taps against ear buds 24 that are measured by sensors 38, button presses, input into device 10 that is relayed to ear buds 24 wirelessly, and/or using other input command gathering techniques. In some arrangements, guidance (coaching) and/or feedback for a routine may be provided both by ear buds 24 (or other wearable equipment) and device 10. For example, guidance and/or feedback may be provided using audio output, visual output, and/or haptic output in ear buds 24 and/or in device 10.

Figure 7:
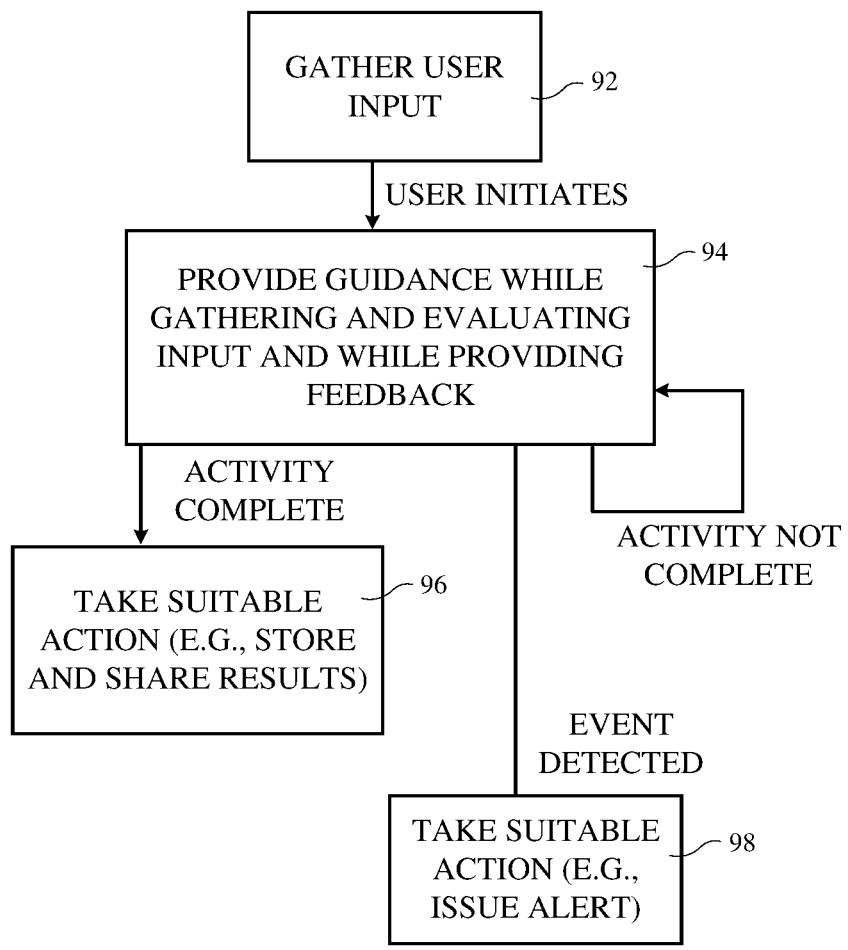
FIG. 7 is a flow chart of illustrative steps involved in using a system having wearable electronic devices such as wireless ear buds in accordance with an embodiment.

FIG. 7 is a flow chart of illustrative operations that may be used in system 8 to guide a user through a guided routine such as an exercise routine (movement routine) while gathering information on the user's movement, analyzing the movement, and providing corresponding feedback based on evaluation of the movement.

During the operations of block 92, a user may launch software in system 8 or otherwise direct system 8 to begin operations involved in monitoring the user's performance. For example, the user may launch an application on device 10 (e.g., by selecting an icon on a touch screen display, clicking on a desktop icon, providing a voice-based device with a voice command, etc.). If desired, the user may provide ear buds 24 with a voice command, tap command, or other input command that launches an exercise routine application on ear buds 24. The launched application or other software may run on control circuitry on ear buds 24 and/or device 10.

In response to user initiation of the exercise routine application or other user initiation of monitoring operations in system 8, control circuitry in system 8 (e.g., in ear buds 24 and/or device 10) can provide a user with exercise routine guidance (block 94). The guidance (coaching) may be audible, visible, and/or haptic and may involve text, spoken commands, diagrams, videos, prerecorded audio clips, and/or other information that helps guide the user through the routine. For example, the guidance may include an overview of the goals of the routine, information on suitable preparation for the routine (e.g., preparatory head movements and body stance), and real-time guidance such as step-by-step directions provided during the routine.

While providing the user with exercise routine guidance during the operations of block 94, the control circuitry in system 8 may use sensors 38 and/or other sensing circuitry in system 8 to gather sensor measurements, may evaluate this input (e.g., to evaluate user performance of an exercise routine by comparing user head poses to a predetermined sequence of head poses associated with the exercise routine), and may provide corresponding feedback. The feedback that is provided may be provided by ear buds 24 and/or device 10 and may be audible, visual, and/or haptic. If no activity is detected, the monitoring and analysis operations of block 94 may continue.

If an undesired health condition is detected (e.g., the user is determined to be out of breath or in distress) or if other conditions are detected that indicate that the exercise should be terminated, suitable actions may be taken during the operations of block 98 (e.g., an alert may be issued for the user, exercise guidance may be terminated, etc.).

If it is determined that the exercise routine has been completed, suitable action may be taken during the operations of block 96. For example, the user may be provided with a completed-routine performance report, a performance report may be uploaded to an online service (e.g., for sharing with other members of the service or for private storage), the user may be provided with tips for future routines (e.g., "next time roll slower"), or other information related to the completion of the exercise routine or other activity of block 94 may be provided to the user.

The foregoing is merely illustrative and various modifications can be made to the described embodiments. The foregoing embodiments may be implemented individually or in any combination.

What is claimed is:

1. An electronic device that is configured to be worn by a user, comprising:
    a housing;
    wireless communication circuitry in the housing that is configured to communicate with additional wireless communication circuitry in an additional electronic device, wherein the wireless communication circuitry is configured to receive sensor measurements from the additional wireless communication circuitry;
    control circuitry in the housing that is configured to evaluate user performance of an exercise routine based on at least the sensor measurements; and
    a display in the housing, wherein the display is configured to provide visual instructions for the exercise routine.

2. The electronic device defined in claim 1, further comprising:
    a speaker that is configured to provide audible feedback based on the evaluation of the user performance.

3. The electronic device defined in claim 1, further comprising:

a speaker that is configured to provide audible instructions for the exercise routine.

4. The electronic device defined in claim 3, wherein the audible instructions comprise verbal commands.

5. The electronic device defined in claim 3, wherein the audible instructions comprise a chime.

6. The electronic device defined in claim 1, wherein the exercise routine is a head movement routine in which the user intentionally places their head in various stretch positions.

7. The electronic device defined in claim 6, wherein the various stretch positions include a left head tilt, a right head tilt, a forward head tilt, and a back head tilt.

8. The electronic device defined in claim 1, wherein the visual instructions for the exercise routine comprise visual pose guidance.

9. An electronic device that is configured to be worn by a user, comprising:
- a housing;
- wireless communication circuitry in the housing that is configured to communicate with additional wireless communication circuitry in an additional electronic device, wherein the wireless communication circuitry is configured to receive sensor measurements from the additional wireless communication circuitry;
- control circuitry in the housing that is configured to evaluate user performance of an exercise routine based on at least the sensor measurements; and
- a display in the housing, wherein the display is configured to provide visual feedback based on the evaluation of the user performance.

10. The electronic device defined in claim 1, wherein the additional electronic device is an ear bud.

11. The electronic device defined in claim 1, further comprising:
- an orientation sensor configured to obtain additional sensor measurements, wherein the control circuitry is configured to evaluate the user performance of the exercise routine based on the sensor measurements and the additional sensor measurements.

12. An electronic device, comprising:
- a housing;
- wireless communication circuitry in the housing that is configured to wirelessly receive first sensor measurements from an ear bud;
- an orientation sensor in the housing that is configured to obtain second sensor measurements;
- a display in the housing that is configured to provide visual instructions for an exercise routine; and
- control circuitry in the housing that is configured to evaluate user performance of the exercise routine based on the first and second sensor measurements.

13. The electronic device defined in claim 12, wherein the visual instructions for the exercise routine comprise visual pose guidance.

14. The electronic device defined in claim 12, wherein the display is configured to provide visual feedback based on the evaluation of the user performance.

15. The electronic device defined in claim 14, wherein the visual feedback comprises a performance grade.

* * * * *